United States Patent
Van Gompel et al.

(10) Patent No.: US 6,240,569 B1
(45) Date of Patent: Jun. 5, 2001

(54) DISPOSABLE MENSTRUAL PANTY

(75) Inventors: Paul Theodore Van Gompel, Hortonville; Joyce Ann Damico; Jacqueline Ann Gross, both of Neenah; Veronica Maria Lingnowski, Menasha; Patricia Ann Mitchler; Gregory John Rajala, both of Neenah; Shelley Rae Rasmussen, Oshkosh; Mark Scott Schrading, Kaukauna; Paul Daniel Suke, Appleton; Jody Dorothy Suprise, Neenah, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 892 days.

(21) Appl. No.: 08/745,303

(22) Filed: Nov. 12, 1996

Related U.S. Application Data

(63) Continuation of application No. 08/263,229, filed on Jun. 21, 1994, now abandoned, which is a continuation-in-part of application No. 08/112,783, filed on Aug. 31, 1993, now abandoned.

(51) Int. Cl.[7] .................................................. A41D 3/00
(52) U.S. Cl. ................................ 2/400; 2/408; 604/385.1
(53) Field of Search ........................... 2/111, 112, 400, 2/401, 402, 403, 404, 405, 406, 407, 408; 604/385.1, 385.2, 395, 396

(56) References Cited

U.S. PATENT DOCUMENTS

| | | |
|---|---|---|
| D. 330,590 | 10/1992 | Pressley et al. ........................ D24/126 |
| 1,458,082 | 6/1923 | Stein . |
| 1,494,044 | 5/1924 | Ward et al. . |
| 1,544,312 | 6/1925 | Gray . |
| 1,830,528 | 11/1931 | Cohon .................................... 2/224 |

(List continued on next page.)

FOREIGN PATENT DOCUMENTS

| | | | |
|---|---|---|---|
| 0054859/90 | 11/1990 | (AU) . | |
| 0072696/91 | 9/1991 | (AU) . | |
| 2014129 | 9/1991 | (CA) . | |
| 825532 | 11/1951 | (DE) | ............................. A61F/13/16 |
| 0033569 | 8/1981 | (EP) | .............................. A41B/9/00 |
| 0187728 B1 | 7/1986 | (EP) . | |
| 0184392 A2 | 9/1986 | (EP) . | |
| 0263665 A2 | 4/1988 | (EP) . | |
| 0403832 A1 | 12/1990 | (EP) . | |
| 0407100 A1 | 1/1991 | (EP) . | |
| 0437771 A2 | 7/1991 | (EP) . | |
| 0452951 A1 | 10/1991 | (EP) . | |
| 0456885 A1 | 11/1991 | (EP) . | |
| 0471114 | 2/1992 | (EP) | ............................. A61F/13/15 |
| 0481092 A1 | 4/1992 | (EP) . | |

(List continued on next page.)

*Primary Examiner*—Gloria M. Hale
(74) *Attorney, Agent, or Firm*—Donald L. Traut; Mark L. Davis; Michael L. Winkelman

(57) ABSTRACT

A three dimensional disposable panty for holding a sanitary pad. The panty may have elasticized leg and waist openings and be stretchable about the hip and stomach regions of a user. The panty provides backup leakage protection to the sanitary pad. The panty includes an absorbent barrier composite positioned in the crotch area and extending into the body of the disposable panty front and back and over the leg elastics to trap pad leakage inside the pant and prevent liquid strike through onto outer clothing and bed linen.

45 Claims, 3 Drawing Sheets

U.S. PATENT DOCUMENTS

| | | | |
|---|---|---|---|
| 1,929,363 | 10/1933 | Long | 2/224 |
| 2,102,359 | 12/1937 | Frieman | 128/289 |
| 2,166,012 | 7/1939 | Maida | 2/224 |
| 2,175,786 | 10/1939 | Smarr | 128/288 |
| 2,206,412 | 7/1940 | Levy | 2/46 |
| 2,252,019 | 8/1941 | Meinecke et al. | 128/291 |
| 2,252,992 | 8/1941 | Steiner | 128/284 |
| 2,299,446 | 10/1942 | White | 128/288 |
| 2,397,641 | 4/1946 | Blair | 2/43 |
| 2,435,945 | 2/1948 | Redmond | 2/224 |
| 2,502,772 | 4/1950 | Winstead | 154/106 |
| 2,538,596 | 1/1951 | Sheridan | 2/224 |
| 2,748,772 | 6/1956 | Titone et al. | 128/288 |
| 2,954,770 | 10/1960 | Roth | 128/288 |
| 3,038,474 | 6/1962 | Harwood et al. | 128/288 |
| 3,087,495 | 4/1963 | Hart | 128/528 |
| 3,098,484 | 7/1963 | Younger | 128/291 |
| 3,142,301 | 7/1964 | Erteszek | 128/528 |
| 3,162,196 | 12/1964 | Salk | 128/287 |
| 3,237,625 | 3/1966 | Johnson | 128/288 |
| 3,288,141 | 11/1966 | Mathison et al. | 128/228 |
| 3,312,981 | 4/1967 | McGuire et al. | 2/224 |
| 3,368,563 | 2/1968 | Scheier | 128/288 |
| 3,386,446 | 6/1968 | Sloan | 128/528 |
| 3,397,696 | 8/1968 | Rickard | 128/288 |
| 3,424,162 | 1/1969 | Parravicini | 128/288 |
| 3,488,778 | 1/1970 | Goujon et al. | 2/224 |
| 3,489,149 | 1/1970 | Larson | 128/288 |
| 3,530,859 | 9/1970 | Heimowitz | 128/284 |
| 3,580,252 | 5/1971 | Delort | 128/290 |
| 3,599,638 | 8/1971 | Rickard | 128/288 |
| 3,599,640 | 8/1971 | Larson | 128/286 |
| 3,604,015 | 9/1971 | Dove | 2/224 |
| 3,608,551 | 9/1971 | Seijo | 128/288 |
| 3,613,686 | 10/1971 | DeWoskin | 128/288 |
| 3,613,687 | 10/1971 | Kennedy | 128/288 |
| 3,636,953 | 1/1972 | Benevento | 128/291 |
| 3,658,064 | 4/1972 | Pociluyko | 128/287 |
| 3,663,962 | 5/1972 | Burger | 2/224 |
| 3,687,141 | 8/1972 | Matsuda | 128/288 |
| 3,720,212 | 3/1973 | Kaupin | 128/288 |
| 3,756,878 | 9/1973 | Willot | 156/70 |
| 3,768,481 | 10/1973 | Shibata | 128/288 |
| 3,816,209 | 6/1974 | De Wokosin et al. | 156/251 |
| 3,828,367 | 8/1974 | Bourgeois | 2/224 A |
| 3,828,785 | 8/1974 | Gamm et al. | 128/288 |
| 3,852,828 | 12/1974 | Silverstein | 2/224 A |
| 3,882,871 | 5/1975 | Taniguchi | 128/287 |
| 3,920,018 | 11/1975 | Schaar | 128/287 |
| 4,022,212 | 5/1977 | Lovison | 128/288 |
| 4,031,568 | 6/1977 | Huff | 2/406 |
| 4,033,801 | 7/1977 | Gros | 156/70 |
| 4,044,769 | 8/1977 | Papajohn | 128/288 |
| 4,067,068 | 1/1978 | Bregstein et al. | 2/406 |
| 4,122,552 | 10/1978 | Tedford | 2/78 R |
| 4,145,763 | 3/1979 | Abrams et al. | 2/403 |
| 4,196,245 | 4/1980 | Kitson et al. | 428/198 |
| 4,205,679 | 6/1980 | Repke et al. | 128/287 |
| 4,227,531 | 10/1980 | McLeod | 128/288 |
| 4,236,257 | 12/1980 | Williams et al. | 2/406 |
| 4,241,462 | 12/1980 | Tagawa et al. | 2/406 |
| 4,244,059 | 1/1981 | Pflaumer | 2/400 |
| 4,244,367 | 1/1981 | Rollenhagen | 128/288 |
| 4,285,342 | 8/1981 | Mesek | 128/287 |
| 4,300,241 | 11/1981 | Shaull | 2/400 |
| 4,302,853 | 12/1981 | Mesek | 2/402 |
| 4,327,448 | 5/1982 | Lunt | 2/404 |
| 4,338,939 | 7/1982 | Daville | 128/286 |
| 4,344,999 | 8/1982 | Gohike | 428/212 |
| 4,351,340 | 9/1982 | McLeod | 128/288 |
| 4,352,356 | 10/1982 | Tong | 128/288 |
| 4,355,425 | 10/1982 | Jones et al. | 2/402 |
| 4,407,284 | 10/1983 | Pieniak | 604/385 |
| 4,411,660 | 10/1983 | Dawn et al. | 604/396 |
| 4,425,128 | 1/1984 | Motomura | 604/381 |
| 4,427,408 | 1/1984 | Karami et al. | 604/393 |
| 4,430,086 | 2/1984 | Repke | 604/385 |
| 4,499,139 | 2/1985 | Schortmann | 428/245 |
| 4,501,792 | 2/1985 | Holemes et al. | 428/299 |
| 4,522,874 | 6/1985 | Pommez | 428/284 |
| 4,536,181 | 8/1985 | Cook | 604/387 |
| 4,555,245 | 11/1985 | Armbruster | 604/396 |
| 4,555,811 | 12/1985 | Shimalla | 2/51 |
| 4,560,381 | 12/1985 | Southwell | 604/396 |
| 4,579,556 | 4/1986 | McFarland | 604/384 A |
| 4,586,199 | 5/1986 | Birring | 2/401 |
| 4,597,110 | 7/1986 | Smith, Sr. et al. | 604/385 A |
| 4,610,680 | 9/1986 | LeFleur | 604/385 A |
| 4,610,681 | 9/1986 | Strohbeen et al. | 604/396 |
| 4,612,674 | 9/1986 | Hashimoto | 2/406 |
| 4,615,051 | 10/1986 | Hashimoto | 2/406 |
| 4,615,695 | 10/1986 | Cooper | 604/385 A |
| 4,619,649 | 10/1986 | Roberts | 604/396 |
| 4,629,643 | 12/1986 | Curro et al. | 428/131 |
| 4,630,320 | 12/1986 | Van Gompel | 2/406 |
| 4,636,207 | 1/1987 | Buell | 604/370 |
| 4,639,949 | 2/1987 | Ales et al. | 2/400 |
| 4,641,381 | 2/1987 | Heran et al. | 2/400 |
| 4,642,818 | 2/1987 | Dehnert et al. | 2/400 |
| 4,642,819 | 2/1987 | Ales et al. | 2/400 |
| 4,646,362 | 3/1987 | Heran et al. | 2/400 |
| 4,655,760 | 4/1987 | Morman et al. | 604/385 A |
| 4,664,663 | 5/1987 | Brier | 604/387 |
| 4,671,793 | 6/1987 | Hults et al. | 604/385 R |
| 4,674,135 | 6/1987 | Greene | 2/400 |
| 4,677,695 | 7/1987 | Van Gompel et al. | 2/79 |
| 4,690,681 | 9/1987 | Haunschild et al. | 604/396 |
| 4,695,278 | 9/1987 | Lawson | 604/385 A |
| 4,695,279 | 9/1987 | Steer | 604/397 |
| 4,698,855 | 10/1987 | Hicks | 2/402 |
| 4,718,902 | 1/1988 | Bonito | 604/396 |
| 4,729,131 | 3/1988 | Thygesen | 2/400 |
| 4,735,622 | 4/1988 | Acuff et al. | 604/361 |
| 4,736,468 | 4/1988 | Efird et al. | 2/400 |
| 4,743,239 | 5/1988 | Cole | 604/385 R |
| 4,743,241 | 5/1988 | Igaue et al. | 604/385 |
| 4,745,636 | 5/1988 | Lunt | 204/402 |
| 4,747,846 | 5/1988 | Boland et al. | 604/38 A |
| 4,771,483 | 9/1988 | Hooreman et al. | 2/237 |
| 4,813,950 | 3/1989 | Branch | 604/396 |
| 4,838,886 | 6/1989 | Kent | 604/392 |
| 4,880,424 | 11/1989 | Rautenberg | 604/396 |
| 4,883,480 | 11/1989 | Huffman et al. | 604/385.1 |
| 4,883,481 | 11/1989 | Blanchard | 604/385.1 |
| 4,898,594 | 2/1990 | Cottenden | 604/397 |
| 4,909,804 | 3/1990 | Douglas, Sr. | 604/385.2 |
| 4,916,005 | 4/1990 | Lippert et al. | 428/192 |
| 4,928,323 | 5/1990 | Nathan | 2/406 |
| 4,932,949 | 6/1990 | Thygesen et al. | 604/386 |
| 4,932,950 | 6/1990 | Johnson | 604/392 |
| 4,938,753 | 7/1990 | Van Gompel et al. | 604/385.2 |
| 4,938,757 | 7/1990 | Van Gompel et al. | 604/396 |
| 4,940,463 | 7/1990 | Leathers | 604/396 |
| 4,940,464 | 7/1990 | Van Gompel et al. | 604/396 |
| 4,950,264 | 8/1990 | Osborn, III | 604/385.1 |
| 4,960,414 | 10/1990 | Meyer | 604/395 |
| 5,019,067 | 5/1991 | Simmons | 604/385.2 |
| 5,031,248 | 7/1991 | Kemper | 2/406 |
| 5,055,103 | 10/1991 | Nomura et al. | 604/385.2 |
| 5,062,839 | 11/1991 | Anderson | 604/385.1 |
| 5,074,854 | 12/1991 | Davis | 604/385.1 |

| | | | |
|---|---|---|---|
| 5,080,741 | 1/1992 | Nomura et al. ................... 156/201 |
| 5,087,253 | 2/1992 | Cooper ............................. 604/385.1 |
| 5,087,254 | 2/1992 | Davis et al. ....................... 604/386 |
| 5,092,861 | 3/1992 | Nomura et al. ................. 604/385.2 |
| 5,098,422 | 3/1992 | Davis et al. ..................... 604/385.1 |
| 5,137,600 | 8/1992 | Barnes et al. ..................... 162/115 |
| 5,147,347 | 9/1992 | Huang et al. ..................... 604/390 |
| 5,158,819 | 10/1992 | Goodman et al. ................. 428/131 |
| 5,163,932 | 11/1992 | Nomura et al. ................. 604/385.2 |
| 5,171,239 | 12/1992 | Igaue et al. ..................... 604/385.2 |
| 5,188,627 | 2/1993 | Igaue et al. ..................... 604/385.2 |
| 5,192,606 | 3/1993 | Proxmire et al. ................... 428/284 |
| 5,197,960 | 3/1993 | Nomura ........................ 604/385.2 |
| 5,234,423 | 8/1993 | Alemany et al. ................ 604/385.2 |
| 5,241,710 | 9/1993 | Lockhart ................................ 2/406 |
| 5,449,353 * | 9/1995 | Watanabe et al. .............. 604/385.2 |
| 5,599,339 * | 2/1997 | Horney ............................... 604/387 |
| 5,624,424 * | 4/1997 | Saisaka et al. .................. 604/385.2 |

FOREIGN PATENT DOCUMENTS

| | | | |
|---|---|---|---|
| 0487921 A2 | 6/1992 | (EP) . |
| 0505027 A1 | 9/1992 | (EP) . |
| 0626160 | 11/1994 | (EP) ............... A61F/13/15 |
| 0626161 | 11/1994 | (EP) ............... A61F/13/15 |
| 2112863 | 6/1972 | (FR) . |
| 1062550 | 3/1967 | (GB) . |
| 1144674 | 3/1969 | (GB) . |
| 1198902 | 7/1970 | (GB) . |
| 1356465 | 6/1974 | (GB) . |
| 1520740 | 8/1978 | (GB) . |
| 2112268A | 7/1983 | (GB) . |
| 2124072A | 2/1984 | (GB) . |
| 2185678 | 7/1987 | (GB) ............... A41B/9/04 |
| 2189133A | 10/1987 | (GB) . |
| 2234157A | 1/1991 | (GB) . |
| 2235125A | 2/1991 | (GB) . |
| 2239783A | 7/1991 | (GB) . |
| 2240462A | 8/1991 | (GB) . |
| 2241871A | 9/1991 | (GB) . |
| 2242348A | 10/1991 | (GB) . |
| 2242610A | 10/1991 | (GB) . |
| 2242821A | 10/1991 | (GB) . |
| 2244201A | 11/1991 | (GB) . |
| 2244422A | 12/1991 | (GB) . |
| 2244909A | 12/1991 | (GB) . |
| 2245149A | 1/1992 | (GB) . |
| 2248380A | 4/1992 | (GB) . |
| 2249712A | 5/1992 | (GB) . |
| 2253131A | 9/1992 | (GB) . |
| 2254997A | 10/1992 | (GB) . |
| 2257347A | 1/1993 | (GB) . |
| 4-0092222 | 6/1992 | (JP) . |
| 4-0166150 | 6/1992 | (JP) . |
| 4-0117618 | 10/1992 | (JP) . |
| 4-0289201 | 10/1992 | (JP) . |
| 4-0364845 | 12/1992 | (JP) . |
| 4-0371147 | 12/1992 | (JP) . |
| 4-0371148 | 12/1992 | (JP) . |
| 5-192366 | 8/1993 | (JP) . |
| WO 80/0001133 | 6/1980 | (WO) . |
| WO 88/0007337 | 10/1988 | (WO) . |
| WO 89/0007923 | 9/1989 | (WO) . |
| WO 91/0019845 | 12/1991 | (WO) . |
| WO 92/0000051 | 1/1992 | (WO) . |
| WO 93/17648 | 9/1993 | (WO) . |
| WO 94/01070 | 1/1994 | (WO) . |

\* cited by examiner

DISPOSABLE MENSTRUAL PANTY

This application is a Continuation of Ser. No. 08/263,229 filed Jun. 21, 1994, now abandoned which is a Continuation-In-Part of Ser. No. 08/112,783 filed Aug. 31, 1993, now abandoned.

FIELD OF THE INVENTION

This present invention relates to undergarments in general, and more specifically to women's disposable undergarments having a fluid repellent region and an absorbent layer to be used with a woman's normal feminine care protection during her menstrual period.

BACKGROUND OF THE INVENTION

Regular undergarments in current use are made of cotton and/or synthetic materials. The cotton and synthetic panties typically do not offer barrier protection. Often the synthetic panties have a cotton lined crotch to absorb vaginal discharges or perspiration. The absorbent/barrier properties of regular undergarments are minimal such that any vaginal discharge and/or heavy perspiration may strike through onto outer clothing (i.e., penetration of liquid from the interior to the exterior of the panty.)

Panty liners and feminine care sanitary napkins or pads used with regular undergarments have polyethylene backings that provide some barrier properties needed to prevent liquid strike through. However, if the vaginal discharge extends to the sides or the ends of the pads it can leak onto the undergarment. This leakage can stain the undergarment. Depending upon the amount of leakage, liquid may strike through or go around the undergarment to stain outer clothing and/or bedding. Women with heavy periods often use one or more maxi pads, double pads and/or tampons alone, or in combination, and change these pads and tampons frequently to prevent embarrassing, messy leakage and/or staining of outer clothing. In some cases, during their heaviest flow days, women will restrict their activities and stay home.

A majority of women experience some leakage of menses from their pads to their undergarments. This varies from being limited to a small number of pads leaking onto only the undergarment during light flow to leakage onto the wearer's outer clothing on almost half the pads worn during heavy flow. Normally this leakage occurs at the side of the product, although end leakage is also a problem. Placement of maxi pads and overnight pads in the crotch of regular undergarments shows that, at best, the pads lay on the leg elastic and, at worst, overhang the leg elastics. This causes side leakage onto the undergarment and possibly onto outer clothing. Typical leakage from the pads is caused by poor fit of the pad to the body, improper positioning of the pad by the user and lack of absorbency. Leakage from the undergarment onto the outer clothing is due to incompatibility between the pad width and the panty crotch width and lack of barrier properties in the panty material around the edge portion of the pad.

SUMMARY OF THE INVENTION

Briefly, this invention describes a three dimensional, disposable, discrete panty with fully elasticized leg and waist openings that is circumferentially stretchable about the hip and stomach regions and which provides back-up leakage protection to feminine care products. It is particularly useful during the wearer's menstrual period, normally occurring in non-pregnant women about every four weeks, from menarche to menopause.

The protection benefit is obtained by providing a flexible secondary absorbent associated with the crotch of the undergarment which holds the primary absorbent in proper location for vaginal discharge (menses). The secondary absorbent extends from the crotch into the body of the undergarment front and back and may extend over the leg elastics. This provides an undergarment which is capable of trapping and absorbing the leakage from the pad and preventing liquid strike through onto outer clothing and bed linen.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE PREFERRED EMBODIMENTS

The following detailed description is made in the context of an article including a disposable panty for holding a sanitary pad in place during use. It is readily apparent, however, that the present invention can be employed with other disposable articles, such as feminine tampons, incontinent garments and the like.

Figure 1:
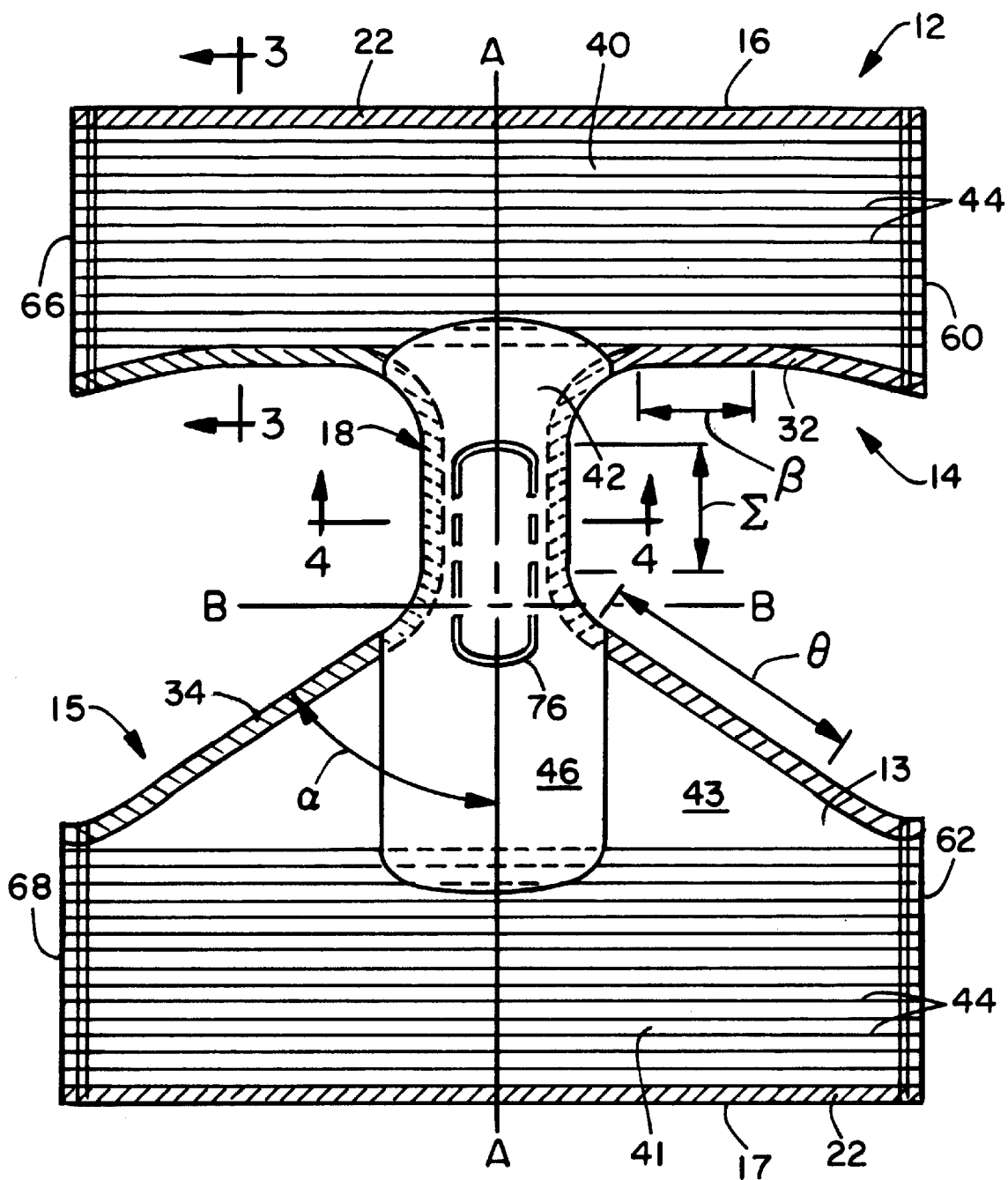
FIG. 1 is a top plan view of a panty article of the present invention in a preassembled flat configuration.

The disposable panty of FIG. 1 illustrates the preferred embodiment of the present invention in a flat configuration prior to assembly. In FIG. 1, a panty 12 is shown having an outer cover 13 which includes a front body portion 14, a back body portion 15, a front waist portion 16, a back waist portion 17, a crotch portion 18, waist liner 26 (not shown), leg liner 38 (not shown) and body liner 80 (not shown).

The outer cover 13 is compliant and soft feeling to the wearer. The outer cover 13 may be liquid pervious, permitting liquids to readily penetrate into its thickness, or impervious, resistent to the penetration of liquids into its thickness. A suitable outer cover 13 may be manufactured from a wide range of materials, such as natural fibers (e.g., wood or cotton fibers), synthetic fibers (e.g., polyester or polypropylene fibers) or from a combination of natural and synthetic fibers or reticulated foams and apertured plastic films.

There are a number of manufacturing techniques which may be used to manufacture the outer cover 13. For example, the outer cover 13 may be woven, nonwoven, such as spunbonded, carded, or the like. A suitable outer cover 13 is carded, and thermally bonded by means well known to those skilled in the fabric art. Alternatively, the outer cover is a spunbond. Ideally, the outer cover is a spunbond polypropylene nonwoven with a wireweave bond pattern having a grab tensile of 19 pounds as measured by ASTM D1682 and D1776, a Taber 40 cycle abrasion rating of 3.0 as measured by ASTM D1175 and Handle-O-Meter MD value of 6.6 grams and CD value of 4.4 grams using TAPPI method T402. Suitably, the spunbond material is available from Kimberly-Clark Corporation, located in Roswell, Ga. The outer cover 13 has a weight from about 0.3 oz. per square yard (osy) to about 2.0 osy and alternatively about 0.7 osy. Preferably, the outer cover of the undergarment has a printed pattern, is colored or is decoratively embossed.

Figure 2:
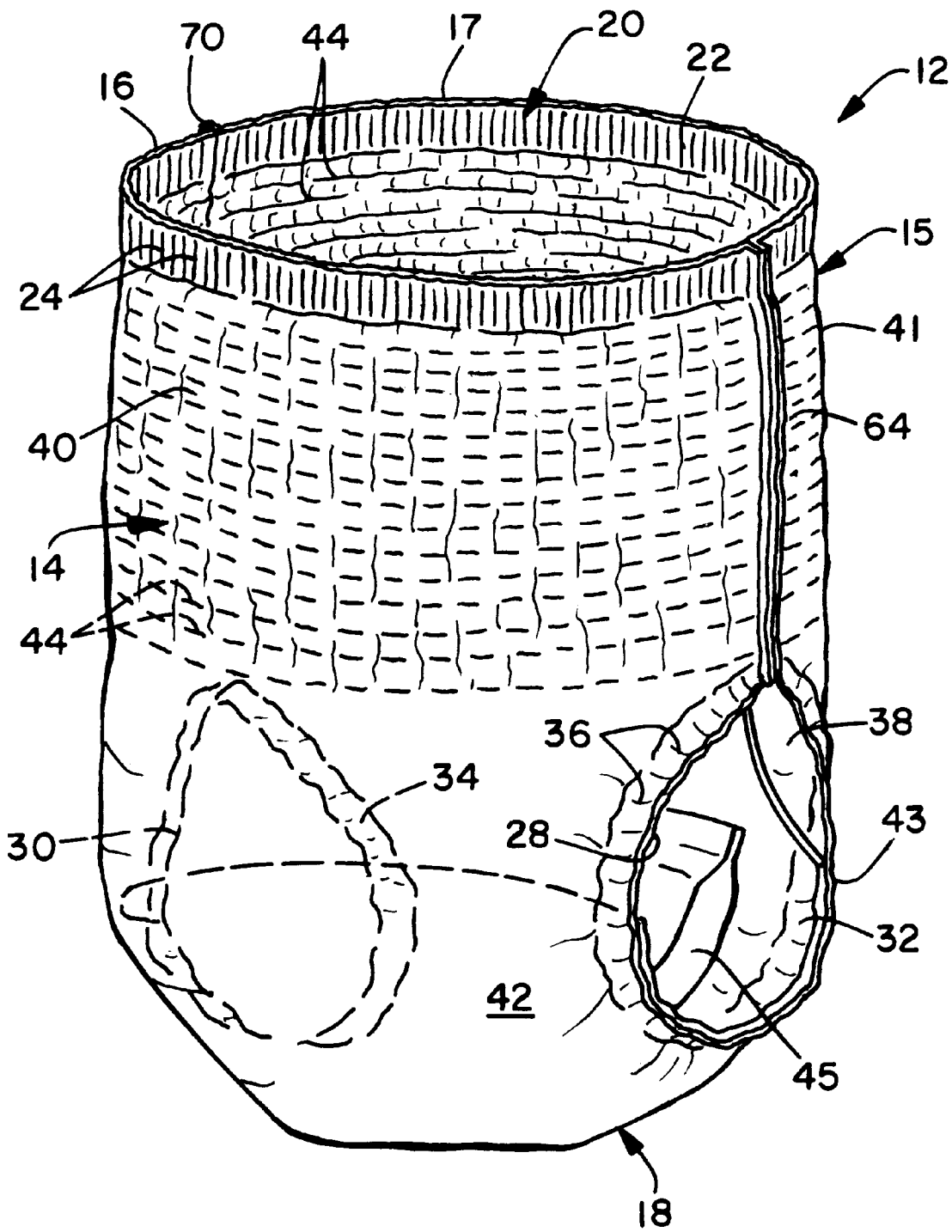
FIG. 2 is a perspective view of a full-sized, disposable menstrual panty of the present invention.
Figure 3:
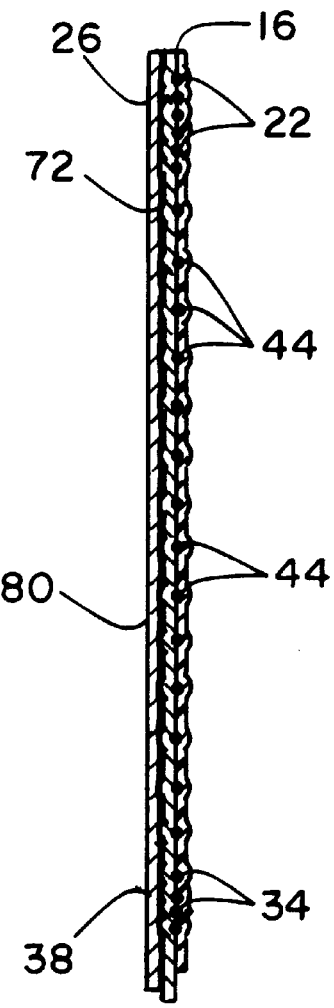
FIG. 3 is a sectioned view taken along view lines 3—3 of FIG. 1 and illustrating the outer cover, liner and elastics.

Referring to FIGS. 1, 2 and 3, an edge 60 of front body portion 14 is assembled with an edge 62 of the back body portion 15 to form a seal 64. Similarly, an edge 66 of the front body portion 14 is assembled with an edge 68 of the back body portion 15 to form a seal 70. The waist portions 16 and 17, when assembled form a waist opening 20 for putting on and taking off the panty 12. The waist opening 20 is surrounded at least in part by a waist elastic 22. The waist elastic 22 is stretched and attached to the waist portion 16. The waist elastic 22 is released after attachment to produce waist folds or pleats 24 to allow expansion of the waist opening 20 so that the panty 12 can fit various sized women. Because users of this invention generally prefer a brief style panty, the waist portion 16 of the panty 12 preferably comes to the navel and is even around the wearer's waist. Having the panty 12 at this height and then drawing in the waist portion 16 with the waist elastic 22 provides a snug fit. Alternative panty styles include bikini (e.g. regular leg cut and french leg cut) and hipster (e.g. regular leg cut or french leg cut).

Referring again to FIGS. 1 and 2, the front body portion 14 and the back body portion 15 together with the crotch portion 18 forms leg openings 28 and 30, respectively, which are generally circular or oval in shape. The leg openings 28 and 30 are each surrounded at least in part by leg elastics 32 and 34, respectively. The leg elastics 32 and 34 are stretched and attached to the front and back body portions 14 and 15 and the crotch portion 18. The elastics are released after attachment to produce leg folds or pleats 36 to allow expansion of the leg openings 28 and 30 to fit various sized legs.

The front body portion 14 is usually divided into a front upper portion 40 and a front lower portion 42. Similarly, the back body portion 15 is divided into a back upper portion 41 and a back lower portion 43. The upper portions 40 and 41 are preferably designed to include body elastics 44 which are capable of stretching to allow the wearer to put on the panty 12 and then readily resume the body elastic's normal contracted form. This ensures a close or snug fit to different body and size forms. A number of body elastics 44 are positioned on both the front and the back portions 40 and 41, respectively, at positions between the waist opening 20 and the leg openings 28 and 30, so that the panty 12 fits the wearer better, particularly around the body. The lower body portions 42 and 43 do not necessarily require elastics. If the outer cover incorporates the body elastic, the basis weight of the outer cover and body elastic laminate may be as high as 5 osy.

In reference to the crotch portion 18 of FIG. 1, the functional total capacity of normal pads worn during the menstrual cycle ranges from about 12 grams to about 63 grams. More typically, the capacity of the pads is above 20 grams. The marketing names associated with such pads include "thin maxi", "maxi", "thick maxi" and "super maxi". These will be referred to as maxi pads. The entire absorbent core normally contained in a maxi pad and which is used during medium to high menstrual flow periods in the panty 12 is the "primary" absorbent 45. The absorbent which is associated with the crotch portion of the current invention is the "secondary" absorbent.

The crotch portion 18 of the panty 12 consists of an absorbent barrier composite 46. The absorbent barrier composite 46 further consists of a liquid barrier 48 and a secondary absorbent 50. In use, secondary absorbent 50 is in surface-to-surface relationship with a primary absorbent placed in panty 12 at crotch portion 18. Preferably, the thickness of the crotch portion 18 is less than about 4 mm. The thickness is measured on a 4 inch (102 mm) square sample (leg elastics removed) with a Mitutoyo Digamatic Indicator using a 3 inch (76 mm) diameter acrylic platen and assembly to produce a pressure of 0.05 psi. The liquid barrier 48 is needed to prevent liquid strike through onto the outer clothing when leakage occurs on the panty 12. The liquid barrier 48 is located on the inside of the crotch portion 18 and consists of a liquid impervious film such as polyethylene. Use of only the film would be hot and uncomfortable, would not be durable enough to withstand changing of pads and would smear any menses which leaked off of the primary absorbent 45. Any film crotch material in the prior art that is elastic is nominally undesirable for the attachment of a pad since the stretch could detach the pad. Therefore, it is desirable to associate the secondary absorbent 50 with a liquid barrier 48 which is nonelastic.

The secondary absorbent 50 should have a liquid capacity great enough to absorb leakage of menses from the primary absorbent 45. The secondary absorbent 50 should preferably have a capacity (described below) and a thickness substantially less than that of the primary absorbent 45, thus providing a nonbulky and flexible fit. The capacity of the secondary absorbent 50 should have a total capacity of about one-half of the primary absorbent 45. Preferably, the secondary absorbent 50 should have a total capacity of at least about 3 grams and not more than 6 grams. More preferably, the total capacity of the secondary absorbent 50 should be from about 4 grams to about 6 grams. However, the basis weight of or the type of secondary absorbent 50 should be adjusted to provide resistance to flexibility of less than around 400 grams.

The absorbent barrier composite of the present invention has a low stiffness. The low stiffness allows the absorbent and barrier to remain attached to the conformable outer cover which conforms to a wide range of body sizes and shapes. Preferably the absorbent barrier composite has a stiffness of less than 400 grams along any axis tested, more preferably less than 300 grams along any axis and less than 100 grams along the axis parallel to the waist opening in the invention.

The secondary absorbent alone will have a stiffness of less than 250 grams and preferably less than 100 grams along any axis and more preferably less than 75 grams along the axis parallel to the waist opening in the invention.

The stiffness of the absorbent barrier composite is measured by peak bending stiffness. Peak bending stiffness is measured by INDA Standard Test method IST 90.3-92 Standard Test Method for Handle-O-Meter Stiffness of Nonwoven Fabrics. The nonwoven to be tested is deformed through a restricted slot opening by a blade, and the required force is measured. This force is a measure of both flexibility and surface friction of the absorbent.

APPARATUS

The test apparatus is an Electronic Digital Read-Out Handle-O-Meter, Model #211-5 equipped with flat plates. The apparatus is available from Thwing-Albert Instrument Company in Philadelphia, Pa.

NUMBER AND PREPARATION OF SAMPLES

For each procedure for this test, five samples should be prepared according to the method described in IST 90.3-92.

For tests involving the absorbent barrier composite, the specimen should include all structural components of the absorbent barrier composite including any materials or methods used to bond that composite together. For tests of the secondary absorbent only, the specimens should be all structural components of the secondary absorbent including materials or methods for bonding that secondary absorbent together.

PROCEDURE

The procedure should be conducted as described in IST 90.3-92. The procedure makes provisions for altering specimen dimensions if resultant grams readout exceeds the 100 gram capacity of the instrument. Reduction in sample size to result in a read-out within the range of the instrument may be necessary for materials falling in the range of the above description. Conduct all such modifications as described in IST 90.3-92 and use the test unit conversion described in section 7.1 of IST 90.3-92. The gap should be set at 0.25 inches (6 mm) as described in section 10.1 of the IST 90.3-92. The absorbent barrier composite should be tested along an axis parallel to the direction in which the absorbent composite was manufactured (so-called machine direction) as well as the axis perpendicular to the direction of the absorbent composite's manufacture (so-called cross direction). In addition each side should be tested along each axis. These steps are detailed in sections 10.1 through 10.10 inclusive in IST 90.3-92.

CALCULATIONS

The maximum reading for each specimen is recorded per IST 90.3-92 section 10.3. The five values are averaged for each axis and side condition tested. The results are reported as maximum grams reading for each specimen. This differs from the millinewtons called for in IST 90.3-92 sections 11 and 12. The average of all five values for each condition is calculated.

The total capacity of the primary absorbent 45 and the secondary absorbent 50 are determined as follows. Any panty adhesive release paper is removed from the pad to be tested. The total capacity of the primary absorbent 45 is determined using the entire napkin minus any release paper. The total capacity of the secondary absorbent 50 is determined using the absorbent barrier composite 46 of the panty 12 and the outer cover 13. The specimen is weighed to the nearest 0.1 gram and acclimated at standard relative humidity and temperature for two hours. The specimen is then submerged in a beaker of sterile saline (0.9% sodium chloride solution obtainable from the Baxter Travenol Company of Deerfield, Ill.), such that the specimen is totally submerged and is not bent or otherwise twisted or folded. The specimen is submerged for 10 minutes. The specimen is removed from the saline and suspended for two minutes in a vertical position to allow the saline to drain out of the specimen. The specimen is then placed body facing surface down onto an absorbent blotter, such as filter paper #631 available from the Filtration Science Corp, Eaton-Dikmena Division of Mount Holly Springs, Pa. A uniform 17.6 grams per square centimeter load is placed over the specimen to squeeze excess liquid out of the specimen. The absorbent blotter is replaced every 30 seconds until the amount of liquid transferred to the absorbent blotter is less than 0.5 grams in a 30 second period. The specimen is then weighed to the nearest 0.1 gram and the dry weight of the specimen is subtracted from the final wet weight. The difference in grams is the total capacity of the specimen.

In construction of the absorbent barrier composite 46, the liquid barrier 48 should retard the movement of the liquid through the absorbent barrier composite 46 by making the barrier liquid resistant to penetration normally encountered under wearing conditions. The composite may be rendered liquid impermeable by any method well known in the art such as coating the secondary absorbent 50 or by securing a separate liquid impermeable material to the secondary absorbent 50. Alternatively, the liquid barrier 48 consists of a liquid impervious film or foam which is pervious to water vapor under normal wearing conditions. More preferred, the liquid barrier 48 has a water vapor transmission rate of at least about 3500 grams/m$^2$/day measured by ASTM E96-92. One example of a suitable film is a 39.4 grams per square meter microporous film produced by Mitsui and sold by Consolidated Thermoplastics (CT) under the tradename of ESPOIR® N-TAF-CT.

The secondary absorbent 50 may be any construction which is generally compressible, conformable, non-irritating to the wearer's skin, capable of absorbing and retaining menstrual fluid. Optionally, the secondary absorbent 50 has first and second opposed faces and includes an absorbent rich layer 51 and a support layer 53. The absorbent rich layer 51 may be manufactured in a wide variety of sizes and shapes (e.g., rectangular, hour-glass, etc.) and from a wide variety of liquid absorbent materials, such as fiberized wood pulp. Examples of other suitable absorbent materials include creped cellulose wadding, absorbent foams, absorbent sponges, super-absorbent polymers, or any equivalent material or combination materials. The support layer 53 may be any construction which is generally resistent to deterioration by liquids while being conformable, non-noisy and capable of holding the absorbent rich layer 51 in place.

Alternatively, the absorbent rich layer 51 can range from 30 to 80 gsm 1:1 blend of northern hardwood pulp and southern softwood pulp. The support layer 53 can be a 12–15 gsm spunbond. The pulp layer is hydroentangled through the spunbond. Alternatively, the combined layers may then be microcreped. The liquid barrier 48 and the secondary absorbent 50 are bonded together using an adhesive 72 add-on of 3 to 7 gsm. Optionally, the absorbent rich layer 51 is bonded to the barrier of the absorbent barrier composite 46. This arrangement permits improved attachment, removal and reattachment of the primary absorbent 45 to the panty 12. The liquid barrier 48 is bonded to the outer cover 13 on the inside of the panty with an adhesive 74 add-on of 5 to 10 gsm. The liquid barrier 48 may be an adhesive film which bonds the secondary absorbent 50 to the outer cover 13. A suitable adhesive for both applications includes, for example, National Starch NS 34-5561 hot melt adhesive which is available from National Starch and Chemical Company located in Bridgewater, N.J.

The width of the crotch portion 18 between the leg elastics 32 and 34 should be wide enough to lay the primary absorbent 45 between the edges without having the primary absorbent 45 obstruct the leg elastics. Primary absorbent 45 is fastened to absorbent barrier composite 46. The primary absorbent may be releasaby attached to the absorbent barrier composite. This allows the leg elastics 32 and 34 to contract and draw up the sides of the crotch to accommodate the depth of the primary absorbent 45 being used and give surface area within the crotch portion 18 to contain leakage from the primary absorbent 45.

Figure 4:
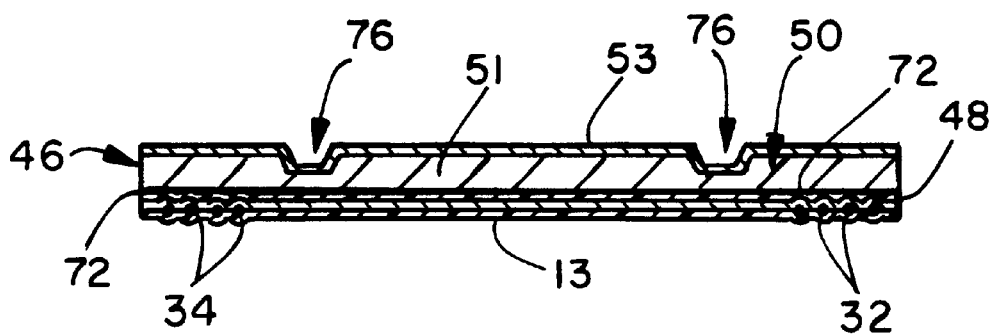
FIG. 4 is a sectioned view taken along view lines 4—4 of FIG. 1 and illustrating the absorbent layer, barrier and outer cover.

The minimum width of the crotch portion 18 should not be so wide as to seem bulky or uncomfortable, but a suitable width is at least about 2.75 inches (70 mm) between the leg elastics. The minimum width is advantageous from about 3 inches (76 mm) to about 3.5 inches (89 mm). Optionally, the width is about 3 inches (76 mm). Preferably, the leg elastics 32 and 34 are from about 0.375 inch (10 mm) to about 0.625 inch (16 mm) wide. More preferably, the width is about 0.5 inch (13 mm). Preferably, ruffle material on the edge of the leg openings 28 and 30 outside the leg elastics 32 and 34 is less than about 0.25 inch (6 mm). More preferably, the ruffle material is less than about 0.125 inch (3 mm). It is most desirable to eliminate the ruffle material from the edge of the leg openings 28 and 30. The overall width of the crotch portion 18 includes the width between the leg elastics 32 and 34, the width of the leg elastics 32 and 34 and the ruffle material outside the leg elastics 32 and 34 to the edge of the leg openings 28 and 30. Preferably, the overall width of the crotch portion 18 should be at least about 4 inches (102 mm). The width of the absorbent barrier composite 46 is sized in relation to the width of the crotch portion 18. Preferably, the width of the composite 46 is at least the width of the crotch portion 18 between the leg elastics 32 and 34. More preferably, the width of the absorbent barrier composite 46 is equivalent to the width of the crotch portion 18 which the composite is mounted across as shown in FIGS. 1 and 4.

The overall length of the absorbent barrier composite 46 should be adequate to extend beyond the ends of the primary absorbent 45 to help prevent liquid strike through at these points when sleeping or sitting. This overall length is at least about 15 inches (382 mm) thus extending beyond the crotch portion 18 along the longitudinal centerline A—A of the panty 12. Alternatively, the length should be in the range of about 15 inches (382 mm) to about 19 inches (484 mm). Optionally, the length of the composite 46 is about 17 inches (433 mm).

The width of the absorbent barrier composite 46 beyond the crotch portion 18 should be at least as wide as the width of the crotch portion 18. The width of the absorbent barrier composite 46 could be narrowed beyond the crotch portion 18 but may compromise the leakage containment. More preferably, the width is from about 5 inches (127 mm) to about 12 inches (306 mm), alternatively from about 5.5 inches (140 mm) to about 7.5 inches (191 mm). Optionally, the width is about 6.5 inches (165 mm). Thus, as seen in FIG. 1, the absorbent barrier composite generally overlies the entirety of the crotch portion including the leg elastics, and is generally confined to the crotch portion, and areas extending generally longitudinaly from the crotch portion.

The present invention contemplates various shapes of the composite 46. One preferred composite has a non-rectangular shape with rounded ends which provides extensive coverage in the seat of the finished panty 12. Another preferred absorbent barrier composite 46 embodiment is rectangular in shape with rounded ends. The essentially rectangular-shaped absorbent barrier composite 46 is more preferred since it can be squared off at the ends to provide a smoother appearance in the back of the panty 12. Line 76 may be embossed or printed on the inner surface of the crotch portion 18 to aid in placement of the primary absorbent 45 by the wearer.

Referring to FIG. 3, the waist elastic 22 is shown covered with a waist liner 26. Referring to FIGS. 3 and 4, the leg elastics 32 and 34 are shown covered by the absorbent barrier composite 46 and a leg liner 38. Referring to FIG. 3, the body elastic 44 is shown covered with a body liner 80. The liner consists of a nonwoven or other soft material for contacting the wearer's skin. As seen in FIG. 4, in preferred embodiments, and allowing for emboss lines, 76, the thickness of secondary absorbent 50 is substantially uniform across the width of the crotch portion. Thus, in the embodiment illustrated in FIG. 4, the thickness of secondary absorbent 50 at the center of the crotch portion is substantially the same as the thickness of the secondary absorbent at the opposing outer edges of the crotch portion.

The position and the shape of the leg openings 28 and 30 are important to avoid tightness in the crotch and groin area of the wearer, to obtain adequate buttocks coverage, and to prevent the panty 12 from tilting forward, i.e. tilting such that the front waist edge dips lower in relationship to the back waist edge. FIG. 1 illustrates the most preferred design for leg fit and buttocks coverage. The shape of the curve across the top of the leg may be considered. If the curve is too deep, the panty 12 will shift downward and backward resulting in a short front waist, increased back length and bagginess in the seat of the panty. This causes the panty 12 to appear tilted when worn as evidenced by an unevenness around the waist of the wearer.

The leg openings 28 and 30 are important to the correct functioning of the panty 12. With the panty 12 laid out flat as in FIG. 1, the majority of the length of the back half of the leg opening is linear preferably forming a straight line. More preferably, the back edge of the leg opening is straight for a length, θ, of at least about 70% of the length of the entire back half. The straight section θ, or linear portion of the back half of the leg opening should form an acute angle with the longitudinal centerline, A—A, of the panty 12. More preferably, the line or linear portion, θ, forms an angle, α, with the centerline A—A of the panty 12 of between about 50° and 65° and most preferably about 60°. The back edge of the leg opening can be essentially linear for a length and can essentially form a 55° angle with the longitudinal centerline of the panty. The majority of the length of the edge of front half of the leg opening including lengths β and ↗ preferably is linear and forms a straight line. More preferably, the lengths of edge β and ↗ of the leg opening is straight for at least about 70% of the length of the front half. The straight section or linear portion β of the front half of the leg opening should form an angle with the centerline of the panty 12 of between about 75° and 110° and most preferably about 90° or essentially perpendicular to the longitudinal centerline A—A.

Likewise, the shape of the arc at the inner groin area is important. If the arc is too shallow, tightness may be experienced at the inner groin area. The preferred narrow crotch width reduces coverage of the buttocks. To compensate for such reduction, the back curve is preferably adjusted downward. The arc between the crotch edge of the leg opening and the back edge of the leg opening should start slightly in front of centerline B—B of the panty 12, see FIG. 1. This allows the leg elastic to be positioned below the lower edge of the buttocks and helps prevent the panty 12 from riding up when walking. This means that the straight portion ↗ of the inner edge of the leg opening is entirely forward of the panty 12 centerline B—B.

The waist, leg and body elastics 22, 32, 34 and 44, respectively, are attached to the panty 12 on the outer cover 13 in generally a stretched state by means known in the art, such as ultrasonic bonded, heat/pressure bonded or adhesively bonded. Materials suitable for elastics include a wide variety including but not limited to elastic strands, yarn rubber, flat rubber, elastic tape, film-type rubber, polyurethane and elastomeric, tape-like elastomeric or foam polyurethane or formed elastic scrim. Each elastic may be unitary, multipart or composite in construction.

The waist elastic 22 is about 0.5 inch (13 mm) wide. The elastic may comprise threads, ribbons, a film or composite.

The threads or ribbons may be multiple and may be applied as a composite. Preferably, the waist elastic is threads, more preferably four threads are used as the elastic and the threads are spaced about 0.17 inch (4.3 mm) apart. The threads may be made of any suitable elastomeric material. One suitable material is spandex such as Lycra® threads available from Dupont located in Wilmington, Del. Suitable waist elastics include threads having a total decitex (g/10000 m) of about 3760 for 0.5 inch (13 mm) wide elastic. Adhesive 74 is used to bond the elastic to the outer cover 13 and the waist liner 26. A suitable adhesive includes, for example, Findley H2096 hot melt adhesive which is available from Findley Adhesives located in Milwaukee, Wis.

The leg elastics 32 and 34 are about 0.5 inch (13 mm) wide. The elastic may comprise threads, ribbons, a film or composite. The threads or ribbons may be multiple and may be applied as a composite. The front and crotch leg elastics may be threads, preferably numbering three threads which are spaced about 0.17 inch (4.3 mm) apart. Back elastics numbering up to six threads should have a width of about 0.75 inch (19 mm) and a spacing of about 0.15 inch (3.8 mm) apart. The threads may be made of any suitable elastomeric material. One suitable material is spandex such as Lycra® threads available from Dupont located in Wilmington, Del. Suitable leg elastics include threads having a total decitex (g/10000 m) of about 3760 for a 0.5 inch (13 mm) wide elastic. Adhesive 74 is used to bond the elastic to the outer cover 13 and to the leg liner 38.

To provide a snug leg fit and to draw up the sides of the crotch portion 18 to form the primary absorbent cradle, the leg elastics 32 and 34 are applied to the outer cover 13 under an elongation of about 250%. Preferably, during the application of the elastics, the elastics 32 and 34 are segmented into multiple segments, each segment being elongated to a different degree and applied to the outer cover 13. In the case of two segments, the front segment is elongated less than the back segment. In the case of three segments, the front and crotch segments are elongated less than the back section. Preferably, the front and crotch segments are elongated to about 150% and the back segment is elongated to about 250%. The segmenting and differing tensions allow easier pad attachment, less tightness in the groin area, and less bunching of the crotch portion 18 caused by high leg elastic retraction. The back leg elastic is under higher elongation to help keep the seat of the panty from creeping up with movement during use.

The body elastics 44 circumferentially surrounding the body portions 14 and 15 of the panty 12 act independently to conform to the contours of various body types and builds. This provides a smooth, snug, and comfortable fit within a given hip size range. Using higher elongation, closer spacing, and higher cross-sectional area in the waist elastic 22 than in the body elastics 44, the panty 12 takes on a rounded shape and provides good waist fit across the waist to hip ratios encountered.

Preferably, in the front body portion the body elastics 44 adjoin both the waist elastic 22 and leg elastics 32 and 34. In a panty 12, the body elastics 44 are about 6.5 inches (166 mm) wide in the front and about 6.0 inches (153 mm) wide in the back. The body elastics 44 are preferably spaced about 0.25 inch (6 mm) apart.

The absorbent barrier composite 46 which extends up the front and/or back body portions toward the waist portion is conformed to the wearer's body by the body elastic 44. The transition from the front and back lower portions to the front and back upper portions is thus smoothed.

The waist elastic 22 is desirably under a greater tension per unit width than the body elastics 44 in the upper body portion 40 to provide the snug waist fit over the range of waist to hip ratios of the various body shapes. In the preferred embodiment, the tension on the waist elastic 22 is coordinated with the tension of the body elastics 44 to form a snug fit about the waist opening while providing a smooth transition from the upper body portion 40 to the waist portion 16. As referred to herine, "unit width" means the dimension of the garment as being acted on by the elastic force, the dimension extending across the elastic transverse to the direction of the retractive force. Thus, for example, in FIG. 2, the "unit width" is the top-to-bottom width of waist elastic 22, or the top-to-bottom width of body elastic 44 between waist elastic 22 and leg elastics 32, 34.

In the front and back body portions 14 and 15, the leg, waist and/or body liners may be expanded to cover the interior of the body portions 14 and 15. The leg, waist and/or body liners may exclude the center crotch portion 18 which is covered by the application of the absorbent barrier composite 46. In the body portions where the absorbent barrier composite 46 overlaps the liner, the composite is applied on top of any liner present so as to contact the wearer.

An acceptable range for the waist elastic tension is from about 380 grams to about 1000 grams. More preferably, the tension at the waist is from about 575 grams to about 750 grams. The preferred leg elastic tension is from about 375 grams to about 1000 grams. More preferably, the tension at the leg is from about 500 grams to about 700 grams. The preferred hip elastic tension is from about 500 grams to about 850 grams. More preferably, the tension at the hip is from about 650 grams to about 750 grams. The waist and leg tensions are determined as follows. The appropriate gauge rod distance is selected from Tables 1 and 2 for a given panty size and desired location measurement. This rod distance is the distance between the top of the upper peg and the bottom of the lower peg on the Chatillon DFG-2 Tensile Tester.

TABLE 1

| | Gauge Rod Distance | |
| Pant Size | Waist | Leg |
| --- | --- | --- |
| 5/6 | 354 mm | 278 mm |
| 7/8 | 392 mm | 306 mm |
| 9/10 | 468 mm | 345 mm |

TABLE 2

| | Gauge Rod Distance | |
| Pant Size | Waist | Leg |
| --- | --- | --- |
| 5/6/7 | 371 mm | 288 mm |
| 8/9/10 | 445 mm | 328 mm |

Measurements are recorded on the tester in kilograms, the HOLD/NORM switch is set at "NORM", the T/C switch is set at "T" (tension). The samples are conditioned and the testing is conducted in a standard laboratory atmosphere of a temperature of 23±2° C. and a relative humidity of 50±5% RH.

For determination of the waist tension, the edge along the bonded seam of the panty 12 is placed over the upper peg of the tester. The panty 12 is allowed to hang freely from the upper peg and the weight of the specimen is tared out.

The lower block is lifted upwards and the opposing waist edge along the bonded seam is placed over the peg of the lower block. The block is lowered until the magnet of the tensile tester locks into place. The tester is activated and timed for two minutes. At two minutes, the tension displayed on the gauge is recorded. The tension in kilograms is converted to grams and the panty 12 is removed.

For determination of leg tension, the edge along the bonded seam near the crotch fold is placed over the upper peg. The panty 12 is allowed to hang freely from the upper peg and the weight of the specimen is tared out.

The lower block is lifted upwards and the bonded seam along the opposing leg opening edge is placed over the peg of the lower block.

The block is lowered until the magnet of the tensile tester locks into place. The tester is activated and timed for two minutes. At two minutes, the tension displayed on the gauge is recorded. The tension in kilograms is converted to grams and the panty 12 is removed. This measurement represents the right leg tension. The test is repeated for the left leg tension.

For determination of hip tension, the top and bottom side seams of the body portion of the panty 12 are placed in the upper and lower 8 inch wide jaws of an Instron Model 1122 equipped with a Sintech software system and the Interactive Materials Analysis Program (IMAP).

The tension program stretches the elastic body portion at a rate of 500 mm/minute until 1000 grams is reached. The crosshead then returns to the starting position and repeats a second cycle. The stress-strain graph can be plotted and tension data points printed at 50, 60, 70, 80, 90% of the full stretch (defined as length at 1000 grams) for first and second load and unload cycles. The tensions were taken from the second cycle unload values at about 85% of full stretch.

The side seams 64 and 70 may be made on the inside or outside of 30 the panty 12 or formed flat against the panty 12 to give a more finished look to the panty 12 and to prevent the seams 64 and 70 from showing through clothing. Optionally, the lateral edges 60, 62, 66 and 68 of the front and back body portions are not overlapped but are formed flat and extend out laterally. The side seams 64 and 70 should be minimal in width while providing sufficient strength to be pulled up and down many times over a 24 hour wear period.

The side seams 64 and 70, respectively, of the outer cover 13 are sealed by means known in the art, such as ultrasonic bonding, stitching, heat/pressure bonding or adhesive bonding. The maximum seam strength attainable is dependent upon materials used, bond pattern, bond width, and process settings of dwell time, power, and pressure. Suitable side seams typically utilize ultrasonic bonding to achieve a seam strength of at least 5 kg.

The seams 64 and 70 may have an unbonded portion outboard of the bonded area to provide for a soft edge to the seam. This unbonded portion can ranged from 2 to 3 mm in width. Alternatively, the entire seam width (bonded portion plus unbonded portion) may be less than about 0.25 inch (6 mm). If the seam is trimmed or cut close to the outer edge of the bond area, a sharp edge is produced along the seam edge which can catch on clothes or be irritating to the wearer's skin.

The panty 12 was compared to panties constructed of cotton and panties having a barrier but no secondary absorbent 50. Seventeen women were retained for this comparison. Each woman wore a selected maxi pad with each panty type until the pad leaked onto that panty type. Loose-fitting cotton shorts were worn by each woman over the panty which could be worn under their normal loose-fitting clothing. At the end of each test, the pad, panty and cotton shorts were collected. The pad, panty and shorts were photographed. The results of the comparison found that cotton panties had leakage to outer garments in 35.3% of the women, panties with barriers but no secondary absorbent 50 had leakage in 41.2% of the women and the panty 12 of this invention had leakage in only 23.5% of the women.

Having thus described the invention in full detail, it will be readily apparent that various changes and modifications may be made without departing from the spirit of the invention. All such changes and modification are contemplated as being within the scope of the present invention, as defined by the following claims.

We claim:

1. A disposable panty, comprising:
   (a) an outer cover having front and back body portions connected by a crotch portion, a transverse centerline extending between said front and back body portions, said front and back body portions being joined to thereby form first and second leg openings, each leg opening having an edge thereabout, including a front edge portion defining the respective leg opening along the front body portion and a first part of the crotch portion, and a back edge portion defining the respective leg opening along the back body portion and a second part of the crotch portion, said back edge portion having a length, and, in a flat blank therefore, extending rearwardly from said crotch portion, along an essentially linear path over a majority of the length of the back edge portion; and
   (b) an absorbent barrier composite mounted to overlie said crotch portion.

2. The disposable panty of claim 1 wherein said absorbent barrier composite is generally confined to said crotch portion, and areas extending generally longitudinally from said crotch portion toward said front and back body portions.

3. The disposable panty of claim 1, said crotch portion having a width, said absorbent barrier composite comprising an impervious layer and a secondary absorbent, and being mounted to said outer cover across the width of said crotch portion.

4. The disposable panty of claim 3 wherein said secondary absorbent comprises a support layer and an absorbent rich layer.

5. The disposable panty of claim 3, the thickness of said secondary absorbent at a center portion of said crotch being substantially the same as corresponding thicknesses of said secondary absorbent at opposing outer edges of said crotch portion.

6. The disposable panty of claim 2 wherein said absorbent barrier composite covers portions of at least one of said front and back body portions.

7. The disposable panty of claim 3 wherein said secondary absorbent has a total absorbent capacity of less than about 6 grams of liquidous exudates.

8. The disposable panty of claim 1, said crotch portion having a width, said absorbent barrier composite comprising a secondary absorbent, said secondary absorbent having an essentially uniform thickness across the width of said crotch portion.

9. The disposable panty of claim 8, said absorbent barrier composite including an impervious layer and a secondary absorbent, and having a stiffness of less than about 400 grams.

10. The disposable panty of claim 1, said length comprising a first length, the front edge portion having a second length, a majority of the second length of the front edge portion being essentially linear.

11. The disposable panty of claim 10, said outer cover carrying at least one waist elastic around said waist opening and thereby forming a gather around the waist, said outer cover further carrying at least one body elastic around said front and back body portions such that said body elastic can stretch in the circumferential direction when said disposable panty is put on, and retract about the body of the wearer when released, to thereby closely conform said body elastic to the shape of the body of the wearer.

12. The disposable panty of claim 11, said body elastic about said disposable panty providing retractive forces, effective about the circumference of said disposable panty, between said waist opening and said leg openings, to thereby provide retractive forces distributed generally uniformly about said disposable panty between said waist opening and said leg openings effective to conform said front and back body portions to the shape of the body of the wearer between said waist elastic and said leg openings.

13. A disposable panty as in claim 1, said length of said back edge portion comprising a first length, each said front edge portion of the respective leg openings having a second length, a majority of the second length of the respective said front edge portion being linear.

14. The disposable panty of claim 13, said crotch portion having a width, said absorbent barrier composite being mounted to said outer cover across the width of said crotch portion, and generally overlying the entirety of said crotch portion.

15. The disposable panty of claim 13, said absorbent barrier composite having an essentially uniform thickness, and a flexibility of less than about 400 grams.

16. A disposable panty as in claim 1, said linear portion of said back edge portion forming an angle of about 50 degrees to about 65 degrees to a longitudinal centerline running through said disposable panty.

17. A disposable panty as in claim 16, said front edge portion having a second length, a substantial part of the length of said front edge portion being linear, said linear portion forming an angle with the longitudinal centerline of said panty of from about 75 degrees to about 110 degrees.

18. The disposable panty of claim wherein said linear portion of said back edge portion of said leg opening in said back body portion of said disposable panty forms an angle of about 55 degrees with the longitudinal centerline of said panty.

19. The disposable panty of claim 17 wherein the linear part of said front edge portion of said leg opening is essentially perpendicular to the longitudinal centerline of said disposable panty.

20. The disposable panty of claim 1 wherein said secondary absorbent comprises a support layer and an absorbent rich layer.

21. The disposable panty of claim 16, said absorbent barrier composite having a flexibility of less than about 400 grams, said absorbent barrier composite including an impervious layer and a secondary absorbent.

22. The disposable panty of claim 21 wherein said secondary absorbent has a stiffness of less than about 250 grams.

23. A disposable panty, comprising:
   (a) an outer cover having front and back body portions connected by a crotch portion, said crotch portion having a width, said front and back body portions being joined to each other to thereby form a waist opening and two leg openings; and
   (b) an absorbent barrier composite mounted over said outer cover across the width of said crotch portion, said absorbent barrier composite having a generally uniform thickness, and having a limited capacity for absorbing no more than about 6 grams of liquidous exudates.

24. The disposable panty of claim 23, said absorbent barrier composite having an impervious layer and a secondary absorbent, said secondary absorbent comprising a support layer and an absorbent rich layer.

25. The disposable panty of claim 24 wherein said absorbent rich layer comprises pulp.

26. The disposable panty of claim 23 wherein said absorbent barrier composite is generally confined to an area of said disposable panty in and adjacent said crotch portion.

27. The disposable panty of claim 26 wherein said absorbent barrier composite covers a portion of at least one of said front and back body portions.

28. The disposable panty of claim 23 wherein said absorbent barrier composite is generally confined to said crotch portion, and areas extending generally longitudinally from said crotch portion toward said front and back body portions.

29. The disposable panty of claim 23, said absorbent barrier composite including an impervious layer and a secondary absorbent, and having a stiffness of less than about 400 grams.

30. The disposable panty of claim 23, said outer cover carrying at least one waist elastic around said waist opening and thereby forming a gather around the waist, said outer cover further carrying at least one body elastic around said front and back body portions such that said body elastic can stretch in the circumferential direction when said disposable panty is put on, and retract about the body of the wearer when released, said body elastic providing retractive forces, effective about the circumference of said disposable panty, between said waist opening and said leg openings, to thereby conform said body elastic to the shape of the body of the wearer.

31. The disposable panty of claim 23, said crotch portion having a width, said absorbent barrier composite being mounted to said outer cover across the width of said crotch portion, and generally overlying the entirety of said crotch portion.

32. A disposable panty adapted to receive a primary absorbent, said primary absorbent having a liquid permeable inner sheet, a liquid impermeable outer sheet and an absorbent member disposed therebetween, said disposable panty comprising:
   a) an outer cover having front and back body portions connected by a crotch portion, said crotch portion having a width, said front and back body portions connected together to form a waist opening and two leg openings;
   b) an absorbent barrier composite mounted over said outer cover across the width of said crotch portion, to which said primary absorbent is attached and which, in use, holds said primary absorbent against the body of a user, said absorbent barrier composite having a flexibility of less than about 400 grams as determined by a peak bending stiffness.

33. The disposable panty of claim 32, said absorbent barrier composite including an impervious layer and a secondary absorbent, said secondary absorbent comprising a support layer and an absorbent rich layer.

34. The disposable panty of claim 32, wherein said absorbent barrier composite is generally confined to said crotch portion, and areas extending generally longitudinally from said crotch portion.

35. The disposable panty of claim 32, said absorbent barrier composite including an impervious layer and a secondary absorbent, the thickness of said secondary absorbent at a center portion of said crotch portion being substantially the same as corresponding thicknesses of said secondary absorbent at opposing outer edges of said crotch portion.

36. The disposable panty of claim 32, said absorbent barrier composite comprising a secondary absorbent, said secondary absorbent having an essentially uniform thickness across the width of said crotch portion.

37. A disposable panty, comprising:
  (a) an outer cover having front and back body portions connected by a crotch portion, said crotch portion having a width, said front and back body portions being joined to each other to thereby form a waist opening and two leg openings;
  (b) leg elastic positioned on said outer cover to form a gather around each said leg opening; and
  (c) an absorbent barrier composite mounted over said outer cover and said leg elastic across the width of said crotch portion.

38. The disposable panty of claim 37, said absorbent barrier composite extending to the edge of said crotch portion.

39. The disposable panty of claim 37, said absorbent barrier composite including an impervious layer and a secondary absorbent, said secondary absorbent comprising a support layer and an absorbent rich layer.

40. The disposable panty of claim 37, said absorbent barrier composite comprising a secondary absorbent, said secondary absorbent having an essentially uniform thickness across the width of said crotch portion.

41. The disposable panty of claim 37, said absorbent barrier composite having a stiffness of less than about 400 grams as determined by a peak bending stiffness.

42. A disposable panty adapted to receive a primary absorbent, said primary absorbent having a liquid permeable inner sheet, a liquid impermeable outer sheet and an absorbent member disposed therebetween, said disposable panty comprising:
  a) an outer cover having front and back body portions connected by a crotch portion, said crotch portion having a width, said front and back body portions connected together to form a waist opening and two leg openings;
  b) an absorbent barrier composite mounted over said outer cover across the width of said crotch portion, to which said primary absorbent is attached and which, in use, holds said primary absorbent against the body of a user, said absorbent barrier composite having an impervious layer and a secondary absorbent, said secondary absorbent having a uniform thickness over the central portion of said crotch portion.

43. The disposable panty of claim 42, said secondary absorbent comprising a support layer and an absorbent rich layer.

44. The disposable panty of claim 43, said secondary absorbent being in surface-to-surface relationship with said primary absorbent.

45. The disposable panty of claim 42, said absorbent barrier composite having a stiffness of less than about 400 grams.

* * * * *

UNITED STATES PATENT AND TRADEMARK OFFICE
CERTIFICATE OF CORRECTION

PATENT NO.    : 6,240,569 B1
DATED         : June 5, 2001
INVENTOR(S)   : Paul T. Van Gompel, Joyce A. Damico, Jacqueline A. Gross, Veronica M. Lingnowski, Patricia A. Mitchler, Gregory J. Rajala, Shelley R. Rasmussen, Mark S. Schrading, Paul D. Suke and Jody D. Suprise It is certified that error appears in the above-identified patent and that said Letters Patent is hereby corrected as shown below:

Column 6,
Line 58, delete "releasaby" and substitute -- refastenably --.

Column 7,
Line 46, insert -- Absorbent barrier composite 46 extends to the edge of crotch portion 18 of the disposable panty. --

Column 8,
Line 3, delete "thickness" and substitute -- thicknesses --.

Column 10,
Line 9, delete "herine" and substitute -- herein --.

Column 11,
Line 34, delete "30".

Column 13,
Line 41, delete "claim" and substitute -- claim 16 --.

Signed and Sealed this

Twenty-fourth Day of December, 2002

JAMES E. ROGAN
*Director of the United States Patent and Trademark Office*